United States Patent [19]

Sessions et al.

[11] 4,258,722
[45] Mar. 31, 1981

[54] DISPOSABLE BIOPSY NEEDLE, PARTICULARLY FOR BONE MARROW SAMPLINGS

[75] Inventors: Robert W. Sessions, Hinsdale; Jerome Jeslis, Chicago; Richard A. Rodzen, Bolingbrook, all of Ill.

[73] Assignee: Ferris Manufacturing Corp., Hinsdale, Ill.

[21] Appl. No.: 969,709

[22] Filed: Dec. 15, 1978

[51] Int. Cl.³ .............................................. A61B 10/00
[52] U.S. Cl. ..................................... 128/753; 128/310
[58] Field of Search ................................ 128/751–754, 128/310

[56] References Cited

U.S. PATENT DOCUMENTS

| | | | |
|---|---|---|---|
| 2,426,535 | 8/1947 | Turkel | 128/754 |
| 2,516,492 | 7/1950 | Turkel | 128/751 |
| 3,175,554 | 3/1965 | Stewart | 128/754 |
| 3,628,524 | 12/1971 | Jamshidi | 128/754 |
| 3,630,192 | 12/1971 | Jamshidi | 128/754 |
| 3,893,445 | 7/1975 | Hofsess | 128/754 |

FOREIGN PATENT DOCUMENTS 422414  9/1974  U.S.S.R. ................................. 128/754

*Primary Examiner*—Kyle L. Howell
*Attorney, Agent, or Firm*—Hill, Van Santen, Steadman, Chiara & Simpson

[57] ABSTRACT

A disposable biopsy needle, particularly for bone marrow biopsy sampling utilizing a metal cannula and stylet structure, and which otherwise may be formed from inexpensive material such as a suitable plastic. Suitable high production techniques, such as injection molding, may then be employed in the production of the remainder of the components of the structure, whereby the final product not only is of excellent design construction for the intended purpose, but also is of exceptionally low cost in manufacture, readily permitting its disposal following a single use.

17 Claims, 8 Drawing Figures

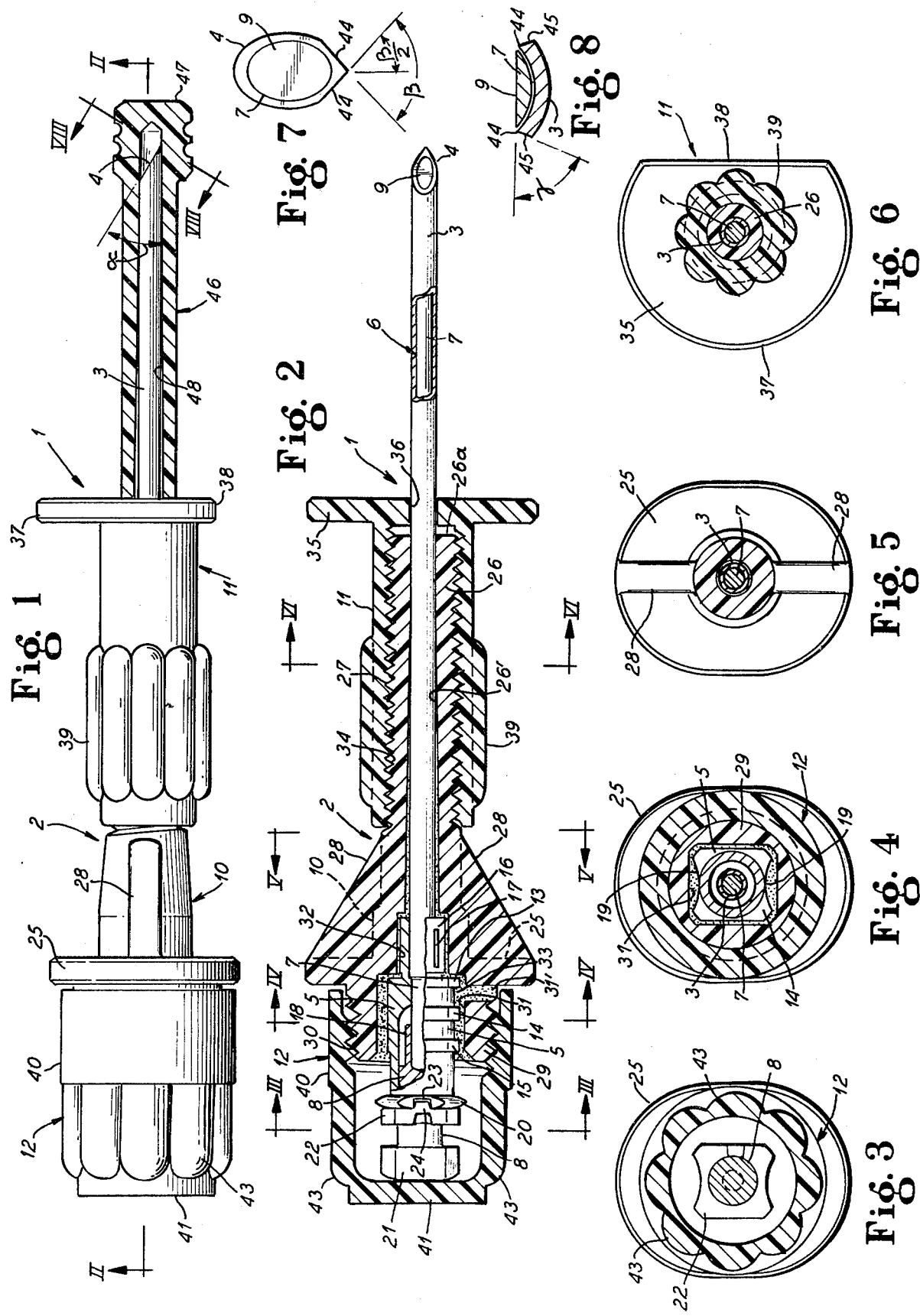

DISPOSABLE BIOPSY NEEDLE, PARTICULARLY FOR BONE MARROW SAMPLINGS

BACKGROUND OF THE INVENTION

The present invention is directed to a biopsy needle, particularly for bone marrow biopsy sampling, in particular a needle structure which is practical for a single use operation.

Biopsy needles have been employed in the medical profession over many years, and in general have been basically metallic structures which will normally include at least a hollow needle or cannula, sharpened at one end for insertion into body tissues, and provided with a detachable stylet which is insertable into the needle for effectively closing the sharpened end thereof during the insertion operation of the needle into the tissue and subject matter to be sampled. Following insertion of the needle assembly, the stylet is removed from the hollow needle and suitable vacuum means, as for example a suitable syringe, is attached to the exposed distal end of the needle for effecting deposit of the biopsy sample in the needle.

To facilitate the use of the needle it may be provided with additional structure readily facilitating the holding of the needle and suitable actuation thereof to provide the desired penetration into the object sample. Where a completely metallic structure is employed, as in the prior art, stainless steel or other suitable metal is employed for the entire structure, usually necessitating suitable joining of the various additional components employed, by soldering, welding, or the like. As a result, needles of this type are relatively costly and are not practical for a single use and disposal.

It has, in recent years, become apparent that the use of equipment, where possible, on a one time basis has many advantages. Studies have shown that operations requiring personnel such as cleaning, sterilizing, packaging, etc. is relatively costly, not to mention the possible danger, irrespective of safety precautions, of cross contamination that is common when units, such as the type here involved, are reused.

BRIEF SUMMARY OF THE INVENTION

The present invention is therefore directed to a biopsy needle, particularly adapted for bone marrow aspiration which, while employing a very efficient structural design, enabling removal of bone marrow with a minimum of time and effort, but which is so designed that, other than the needle and stylet assembly per se, all other structural components associated therewith may be readily and inexpensively fabricated out of suitable material, such as a suitable plastic. By use of such a material, the structural design may be such that the respective plastic components may be readily and effectively fabricated by suitable molding operations as, for example, injection molding, resulting in the production of components that will readily withstand the stresses placed thereon in use, and which due to the nature of the fabrication processes and material employed, may be produced at a very low cost, resulting in a biopsy needle that is completely practical, as to efficiency and low cost, for a one time use, after which it may be thrown away.

In accordance with the invention, the needle or cannula is rigidly secured to a plastic body member, provided at its distal end with an adjustable stop member, by means of which the depth of penetration of the needle may be readily and accurately controlled. The cannula or needle is provided with a cooperable metallic stylet which is detachably engageable with the cannula and is provided with means thereon, interlocking with cooperable means on the cannula, to orient the needle and stylet with respect to relative rotation between the two, thereby providing a desired orientation of the distal end of the stylet with the corresponding end of the cannula. The latter preferably is provided with a pointed end produced by suitable forming operations on the stylet and cannula to dispose their distal end faces in a common plane extending diagonally with respect to the axis of the needle.

Cooperable with the body member is a cap member which is detachably carried by the body member, for example by means of cooperable threads on the respective members. The body member and cap member are so proportioned that when the cap member is in its fully assembled position relative to the body member, it engages the adjacent end of the stylet structure to retain the latter in assembled relation with the cannula, and in particular to maintain the parts in the desired rotary orientation.

The pointed end of the needle-stylet assembly preferably has a specific pointed configuration which provides very efficient penetrating action when in use.

The adjustable stop member enables the surgeon to accurately control the depth of penetration of the pointed end of the structure into the object being sampled.

Following disposition of the needle structure at the desired location for a particular biopsy sampling, the cap member may be removed and the stylet withdrawn. A suitable vacuum-producing device, such as a suitable syringe, may then be attached to the proximal end of the cannula structure for drawing the sample into the needle. Preferably the proximal end of the cannula is provided with a suitable lock connection, such as a standard luer connection, by means of which the mounting of a syringe or other vacuum-producing device can be operatively connected with the proximal end of the cannula.

BRIEF DESCRIPTION OF THE DRAWINGS

In the drawings wherein like reference characters indicate like or corresponding parts:

FIG. 1 may be considered a top plan view of a biopsy needle assembly in accordance with the invention;

FIG. 2 is a sectional view taken approximately on the line II—II of FIG. 1 with the needle structure, per se, shown primarily in elevation;

FIG. 3 is a sectional view taken approximately on the line III—III of FIG. 2;

FIG. 4 is a sectional view taken approximately on the line IV—IV of FIG. 2;

FIG. 5 is a sectional view taken approximately on the line V—V of FIG. 2;

FIG. 6 is a sectional view taken approximately on the line VI—VI of FIG. 2;

FIG. 7 is a plan view of the angular face of the pointed end of the needle and associated stylet structure; and FIG. 8 is a sectional view through the needle point and stylet taken approximately on the line VIII—VIII of FIG. 1.

DETAILED DESCRIPTION OF THE INVENTION

The General Structure

Referring particularly to FIGS. 1 and 2, the disposable biopsy needle in accordance with the present invention comprises two major components, the first being needle and cooperable stylet structures, indicated generally by the numeral 1, constructed of suitable metal, for example, stainless steel, and a body structure indicated generally by the numeral 2 by means of which the device may be manually grasped and actuated in a biopsy sampling operation, and is constructed from suitable material, for example a suitable plastic. The plastic material selected should have the properties of adequate strength and durability for the purposes involved, capable of being readily sterilized, having properties that will readily permit fabrication of the parts by suitable molding processes, for example injection molding, and which is of sufficiently low cost that the overall expense of producing the complete device, including the metal needle structure will be sufficiently low that it is practical to utilize the device for a single biopsy operation following which the structure is thrown away. Thereby sterilization, possible sharpening of the needle point, packaging and storage for reuse are eliminated. In addition, such plastic should be inert to materials of the human body and non-toxic thereto. We have found that a particularly suitable material for the purpose is FDA quality polycarbonate which may be suitably colored as desired or required.

The metallic structure comprises two major parts, the hollow needle or cannula structure 3 which is provided at its distal end with a pointed end configuration 4, and at its proximal end with a hub portion 5. Cooperable therewith is a stylet structure indicated generally by the numeral 6 and comprising an elongated rod-shaped portion 7 having a stylet hub member 8 rigidly secured to its proximal end and terminating at its free distal end in a flat face 9 cooperable with the pointed end 4 of the cannula 3 as hereinafter described in detail.

The body portion 2 comprises three components, a base portion, indicated generally by the reference numeral 10, having adjustably mounted thereon a stop member 11 for determining the depth of insertion of the needle in use, and a cap member 12 which is detachably mounted on the base member 10.

DETAILS OF THE NEEDLE STRUCTURE

Referring particularly to FIGS. 2, 3 and 4, the hub member 5 is of generally tubular construction having a plurality of generally flat, radially extending ribs 13, 14 and 15 with the distal end of the hub having a sleeve portion 16 in which the proximal end of the cannula 3 is disposed, and rigidly secured therein by suitable means, as for example, suitably crimping 17 and soldering. As illustrated in FIG. 2, the stylet rod 7 has its proximal end inserted in a sleeve portion 18 formed on the adjacent end of the stylet hub 8. The remainder of the latter may be of solid construction as illustrated in the drawings. The radially extending ribs 13, 14 and 15 on the hub member 5 are of like configuration, as illustrated in FIG. 4 for the rib 14, and are generally of a square configuration with the upper and lower edges as viewed in FIG. 4 being concave as indicated at 19. The proximal end of the hub member 5 is provided with a terminal flange 20 which likewise has a size and configuration generally corresponding to the ribs 13–15. The stylet hub 8 is provided with two head members, a terminal member 21 and a spaced inner member 22, which have a like configuration, as illustrated in FIG. 3 for the member 22, and which, in turn, substantially correspond to the configuration of the ribs 13–15 and the flange 20 of the hub 5.

As illustrated in FIG. 2, the inner member 22 is adapted to seat on the member 20 of the hub 5 with the two parts being maintained in a predetermined oriented position which will dispose the end face 9 of the stylet in the plane of the corresponding edge of the cannula 3, as illustrated in FIGS. 1 and 2. Such orienting means in the embodiment illustrated comprises a slot 23 formed in the member 20 of the hub 5 and a complemental projection 24 formed on the member 22, as for example by suitably offsetting the adjacent metal of the member 22, as readily apparent from FIG. 2. The member 20 preferably comprises a suitable connecting structure, such as part of a luer lock connection, by means of which a syringe or other device may be firmly connected to the hub 5.

The Body Assembly

The base member 10 in which the needle assembly 1 is rigidly mounted, as illustrated in FIG. 2, 4 and 5, comprises a generally oval shaped plate-like flange or head portion 25 from which a generally tubular shaped stem portion 26 extends, with such stem portion being provided with external threads 27 for the greater portion of its length, extending to the free distal end 26a thereof. Strength and rigidity is provided between the portions 25 and 26 by reinforcing ribs 28, the free outer edges of which extend diagonally from the periphery of the portion 25 to adjacent the threaded portion of the stem. Disposed at the opposite side of the head portion is an axially aligned tubular projection 29 which is provided with external threads 30 thereon.

As illustrated in FIG. 4, the bore 31 in the portion 29 has a generally rectangular configuration of a size to receive the adjacent portions of the hub member 5, with the sleeve 16 of the hub being disposed in a circular bore 32 extending through the head portion 25 and into the stem 26. The needle assembly including the cannula 3 and hub 5 are rigidly secured together by suitable means, such as cement 33, which is disposed in the bores 31 and 32 as well into the space between the cannula 3 and the adjacent side wall of the bore 26' of the stem 26. As illustrated in FIG. 2, preferably the side walls of the bore 26' of the stem adjacent the sleeve 16 taper slightly, forming a space for the receipt of cement, whereby the cannula 3 is bonded to the stem through a sizable portion of its length to provide a very firm mounting of the needle assembly in the base member. To facilitate cementing, the body member may be provided with a radially extending bore 31' intersecting the bore 31, which may be utilized for cement supply, as well as relief for excess cement.

The adjustable stop member 11 is of generally tubular construction and is provided with internal threads 34 which mate with the threads 27 of the stem portion. The distal end of the stop member is provided with an enlargement in the form of a transversely extending flange 35, having an axial bore 36 therein of a size to permit free movement of the cannula 3 therein. The flange 35, as illustrated in FIG. 6, has a generally semicircular configuration with a circular edge 37 and a straight edge 38 at one side forming a chord of the circular configuration. Manual rotation of the stop member 11 relative to the stem 26 is facilitated by longitudinally extending finger engageable peripheral ribs 39 formed on the exterior of the stop member 11. Thus, by rotating the stop member 11 relative to the stem 26 of the base member 11, the stop member may be moved axially along the cannula 3, thereby adjustably moving the flange 35 toward or away from the pointed end of the needle. The flange 35 thus may function as a depth gage or stop for controlling penetration of the needle into and object.

The cap member 12 is of generally cup-shaped configuration, i.e. having tubular side walls 40 closed at its outer end by an end wall 41 and provided adjacent its open end with internal threads 41 adapted to mate with the threads 30 on the member 29 of the base member 10. To facilitate rotating the cap member 12 with respect to the base member 10, the cap member may be provided with longitudinally extending external ribs 43 thereon, which may be readily grasped by the thumb and fingers to permit assembly or removal of the cap member 12 on the member 10. As will be apparent from the reference to FIG. 2, the cap member 12 is so dimensioned that the inner surface of the end wall 41 will engage the adjacent, generally rounded end face of the member 21 of the stylet hub 8 without the open end of the cap member engaging the head 25. This construction permits the cap 12 to be screwed down into firmly engagement with the stylet hub 8, rigidly locking the stylet in interlocked relation with the hub 5 and the cannula 3.

While various configurations of the pointed end 4 of the needle may be utilized as a practical matter, FIGS. 7 and 8 illustrate a particularly effective point configuration for the desired purposes. As illustrated in FIGS. 1, 2 and 7, the end face of the pointed end 4 of the cannula 3 and end face 9 of the stylet are disposed in a common plane which extends diagonally with respect to the axis of the structure. In forming the pointed end of the needle, the stylet is inserted in interlocked relation with the hub of the cannula, accurately aligning the stylet 7 with the cannula, and the free end of the assembly is then formed into the desired shape, for example by cutting and/or grinding. Such operation forms both the end edge of the needle and the end face 9 of the stylet, thus giving the end edge of the needle and the end face 9 of the stylet an oval configuration as illustrated in FIG. 7, with such end edge 4 and end face 9 being disposed in said common plane.

While the pointed configuration of the free end of the needle may be derived solely by the diagonally extending end edge of the cannula, by suitable configuration, the point can be given improved efficiency, as hereinafter described, by the particular configuration illustrated in FIGS. 7 and 8.

In this embodiment the diagonally extending end edge of the cannula will present a generally oval configuration as illustrated in FIG. 7. By a suitable operation, for example grinding, the lowermost edge, as viewed in FIG. 7, at the most extreme end of the cannula is symmetrically formed with respect to the long axis of the oval configuration of the end edge, to provide straight cutting edges 44, which are defined by the walls 45, which intersect on such long axis, providing a very sharp extreme point on the needle. As illustrated in FIG. 7, the side walls 45 have an included angle equal to $\beta$ and thus the angle of each edge, with respect to the long axis of the oval configuration, is equal to $\beta/2$. In like manner, the edges 44 may be so formed that the side edges 45, formed by the grinding operation, are at an angle $\gamma$ with respect to the plane of the end edge 4 of the needle and end face 9 of the stylet, preferably the angle $\beta$ is greater than the angle $\alpha$ illustrated in FIG. 1, between said plane and the axis of the cannula, but less than the angle $\gamma$. A pointed end having a described configuration is very efficient when used on bone and the like. More efficient results are believed to be achieved, for 15' and 18 gauge needles, with an angle $\alpha$ on the order of 30°, an angle $\beta$ on the order of between 60° and 90°, and an angle $\beta$ on the order of 100°.

To protect the needle prior to use, the exposed end of the needle may be suitably encased, for examples by a hollow protective sleeve 46 which is of generally tubular construction, having a closed outer end 47 and provided with a tapered bore 48 of a size to frictionally engage the outer end portion of the needle when inserted into the bore 48. The latter is so dimensioned that the sleeve 46 may be firmly frictionally retained on the needle, whereby it will not inadvertently come off, but at the same time will permit manual removal without difficulty at time of use.

Use of the Needle

Needles in accordance with the present invention will normally be individually packaged in sterilized form in which they may be readily transported, stored, etc. At time of use, the needle assembly is removed from its packaging and the protective sleeve 44 removed from the cannula 3. Following normal preparation, i.e. suitable sterilizing and anesthesia of the object, for example an arm or leg, the assembly, as illustrated, is grasped by the ribs on the adjustable stop member, at the same time bearing on the flange, and the remainder of the structure gripped in the hand, and penetrating pressure applied to the needle, if desired slightly rotating the needle simultaneously therewith by suitable movement of the hand and fingers. When the pointed end of the needle reaches the bone structure, the doctor will be immediately apprised of the fact as such action will be felt in the assembly. With the needle in such position, the stop member 11 may be suitably rotated with respect to the stem 26 to bring the adjacent face of the flange 35 to the external surface of the object, or the location of the skin surface on the needle may be noted, and the needle removed, following which the stop member is rotated to such point.

Once the stop member is so positioned, the exposed portion in the needle thus represents the distance in the flesh between the skin surface and the outer face of the bone involved. With this knowledge, the doctor can then suitably rotate the stop member to move the same toward the base member and thus increasing the effective length of the needle, until the additional increase in length represents the desired penetration of the needle into the bone.

The adjustment of the stop member is of particular importance as unwarranted complications could arise if excessive penetration were made.

When the stop member has been satisfactorily adjusted for the proper depth of penetration, the instrument is grasped with the thumb and forefinger behind the flange of the adjustable stop member and the balance of the instrument secured in the closed hand. This grip gives excellent control and the ability to deliver high thrust and torque to enhance bone penetration. It will be noted that the thrust reaction on the stylet and needle is transmitted directly to the cap member 12.

Likewise, as all the thrust forces on the instrument are transmitted on the axis of the needle and stylet, involving compression forces thereon and on the end wall of the cap member 12, none of the plastic portions of the device are subjected to thrust forces that would tend to break the plastic structure. Torque forces on the stylet 1, as a result of the diagonal end face 9 thereof, is transmitted to the stylet hub 8 and from the latter to the needle hub 5 to the base member 10. Similarly, torque on the needle 3 is transmitted to the needle hub 5 and therefrom to the base member 10.

The pressure and rotation of the assembly is continued until the end of the needle has bored into the bone the desired distance, indicated by the flange 35 reaching the skin surface. With the assembly in such position, the cap 12 is then unscrewed from the base member 10 exposing the proximal end of the needle and stylet assembly, at the same time removing the locking pressure on the stylet hub 8. As a result, the stylet may be manually gripped by the hub 8 and readily withdrawn from the cannula 3. Suitable vacuum means, as for example, a suitable syringe may then be attached to the flange member 20 of the hub 5, following which a marrow sample may be withdrawn into the needle. As previously mentioned, the needle hub, in particular the flange 20 thereof, can be so designed that it conforms to USA standard USA'S regulations, for example conforms to a standard luer lock connection, thereby enabling ready connection of syringes and other devices provided with such type of lock connection.

Following use of the needle, its simplicity and corresponding relative low cost permits a one time use thereof and disposal thereafter, eliminating, cleaning, sterilizing, repackaging and storage problems and attendant expense.

Although we have described our invention by reference to particular illustrative embodiments, many changes and modifications of the invention may become apparent to those skilled in the art without departing from the spirit and scope of the invention. We therefore intend to include within the patent warranted hereon all such changes and modifications as may reasonably and properly be included within the scope of our contribution to the art.

We claim as our invention:

1. In a disposable biopsy needle, particularly for bone marrow biopsy samples, with an elongated plastic, hollow, body member, a hollow needle structure having its proximal end extending through a first end of the hollow body member and its distal end projecting from the hollow body member and terminating in a pointed free end, a stylet structure, in the general form of a rod member, disposed in the hollow needle structure with a distal end operatively closing the adjacent distal end of the needle structure and having a proximal end extending from the corresponding proximal end of the needle structure and lockable thereto to block relative rotation therebetween, an improvement comprising:

a region in the hollow body member having a selected cross section with at least two spaced apart parallel sides;

at least one radially extending rib surrounding a portion of the proximal end of the hollow needle structure and located within said region of said hollow body member, said rib has at least two spaced apart parallel sides;

a layer of adhesive located in said region in the hollow body member and in contact with said radially extending rib to rigidly attach the proximal end of the hollow needle structure to the hollow body member;

a cap threadably receivable onto a set of threads on a second end of the hollow body member, adjacent the proximal end of the stylet structure and rotatable into contact with the proximal end of the stylet structure to lock the stylet structure into a fixed axial position with respect to the elongated hollow body member;

and a stop member threadably mounted on the first end of the hollow body member and axially adjustable therealong by rotation to vary the distance between a distal end thereof and the pointed end of said needle structure, said stop member having an enlargement at said distal end adapted to engage the skin surface of the object from which the sample is to be taken for limiting penetration of the needle structure therein.

2. The disposable biopsy needle according to claim 1, wherein the proximal end of the needle structure includes a connection fitting, for engagement with a cooperable fitting of vacuum producing means for withdrawing bone marrow into the needle structure following removal of the stylet structure.

3. The disposable biopsy needle according to claim 1, wherein the needle and interlocked stylet structures are formed at their distal ends in end faces lying in a common plane diagonally intersecting the axis of said assembled structure and forming said pointed end.

4. The disposable biopsy needle according to claim 3, wherein the extreme distal end of the needle structure is provided with two intersecting external edges, forming a sharp angular point thereon.

5. The disposable biopsy needle according to claim 4, wherein said intersecting edges have an included angle which is symmetrical to the long axis of the oval configuration of the end edge of the needle structure formed by said plane, said included angle being larger than the angle of said plane with the axis of the needle and stylet structures, and smaller than the angle of the side walls, forming said edges, with said plane.

6. The disposable biopsy needle according to claim 4, wherein said plane angle is on the order of 30°, said included angle is on the order of 60° to 90°, and said sidewall angle is on the order of 100°.

7. The disposable biopsy needle according to claim 1, wherein said enlargement on said stop member comprises a generally planar annular shaped flange.

8. The disposable biopsy needle according to claim 7, wherein said stop member is provided, on an external surface, with manually grippable longitudinally extending ribs.

9. The disposable biopsy needle according to claim 7, wherein said cap is generally cylindrical and provided on its external surface with manually grippable longitudinally extending ribs.

10. The disposable biopsy needle according to claim 1, including a radially extending flange adjacent said threads on said second end of the body member.

11. The disposable biopsy needle according to claim 10, wherein said flange has a generally oval configuration, the width at the short axis thereof being approximately equal to the corresponding width dimension of said cap.

12. The disposable biopsy needle according to claim 11, including further two flange-reinforcing ribs extending from said body member to said flange and disposed on the long axis of the oval configuration of said flange.

13. In a disposable, bone marrow biopsy needle having an elongated, molded plastic handle with an axially oriented opening, an elongated cannula with first and second ends and an elongated stylet with first and second ends, the stylet is receivable within the cannula with the respective first and second ends located adjacent one another and lockable to the cannula to prevent relative rotation therebetween, the first ends of the cannula and the stylet are receivable within the axial opening of the plastic handle with the cannula and stylet extending axially from a first end of the plastic handle, an improvement comprising:

at least two planar spaced apart surfaces on the first end of the cannula located adjacent two corresponding surfaces on the axial opening;

a layer of adhesive located between said two surfaces on the axial opening and said two surfaces on the first end of the cannula to rigidly attach the cannula to the handle; and a cap threadably receivable onto a second end of the handle, adjacent the first end of the stylet to lock the stylet against the cannula and prevent axial movement of the stylet with respect thereto, whereby, the second ends of the cannula and stylet may be inserted through flesh to a bone to be biopsied and the handle can be manually rotated simultaneously with the application of force against said cap to cause the second ends of the cannula and the stylet to cut through the bone to provide access to the interior thereof.

14. The improved disposable bone marrow biopsy needle according to claim 13 wherein:

the second ends of the cannula and stylet are formed in a common plane surface oriented at a selected angle and with an elongated eliptical shape.

15. The improved disposable bone marrow biopsy needle according to claim 14 wherein said second end of the cannula is further formed with two symmetrical straight edges at one end of said eliptical shape which come together to form a point and which are at a selected angle with respect to said common planar surface.

16. The improved disposable bone marrow biopsy needle according to claim 14 wherein:

said two planar surfaces located on the axial opening are located adjacent the second end of the molded plastic handle and a substantial portion of the axially oriented opening extending between said two planar surfaces and the first end of the handle is tapered and displays a continually decreasing radius terminating at the first end of the body at a radius corresponding to the extending radius of the cannula and wherein said layer of adhesive extends substantially along said tapered axial opening thereby forming a bond between a substantial portion of the plastic handle and the cannula.

17. The improved disposable bone marrow biopsy needle according to claim 16 including further a means for stopping rotatably adjustable on the handle to alter the exposed length of the cannula thereby limiting the depth that the second ends of the cannula and stylet can penetrate into the flesh and bone.

* * * * *